United States Patent
Bergamaschi et al.

[11] Patent Number: 5,857,062
[45] Date of Patent: Jan. 5, 1999

[54] HEATED RESPIRATORY THERAPY HUMIDIFIER

[75] Inventors: Paolo Bergamaschi, Concordia; Lucio Gibertoni, Mirandola, both of Italy

[73] Assignee: Mallinckrodt Inc., St. Louis, Mo.

[21] Appl. No.: 860,583

[22] PCT Filed: Dec. 27, 1995

[86] PCT No.: PCT/EP95/05145

§ 371 Date: Jul. 1, 1997

§ 102(e) Date: Jul. 1, 1997

[87] PCT Pub. No.: WO96/20747

PCT Pub. Date: Jul. 11, 1996

[30] Foreign Application Priority Data

Jan. 3, 1995 [IT] Italy ................... MI95A0006

[51] Int. Cl.$^6$ .............. A61M 16/00; F24F 6/08; B01D 47/00; A02B 7/10
[52] U.S. Cl. .............. 392/390; 392/395; 261/104; 128/203.16; 128/205.12
[58] Field of Search .............. 392/386, 390, 392/394, 395, 402, 403, 404, 405, 406; 261/100, 101, 102, 104, 105, 106, 107, DIG. 65; 128/203.16, 203.17, 203.26, 203.27, 204.13, 205.12, 205.13

[56] References Cited

U.S. PATENT DOCUMENTS

| | | | |
|---|---|---|---|
| 3,757,082 | 9/1973 | Goicoechea | 392/403 |
| 3,820,540 | 6/1974 | Hirtz et al. | 128/203.27 |
| 3,912,795 | 10/1975 | Jackson | 261/104 |
| 3,982,095 | 9/1976 | Robinson | 392/403 |
| 4,146,597 | 3/1979 | Eckstein et al. | 261/104 |
| 4,155,961 | 5/1979 | Benthin | 261/104 |
| 4,657,713 | 4/1987 | Miller | 128/203.27 |
| 4,943,704 | 7/1990 | Rabenau et al. | 392/386 |
| 5,131,387 | 7/1992 | French et al. | 128/205.12 |
| 5,195,515 | 3/1993 | Levine | 128/203.17 |
| 5,657,750 | 8/1997 | Colman et al. | 128/205.12 |

*Primary Examiner*—Mark H. Paschall
*Assistant Examiner*—Sam Paik
*Attorney, Agent, or Firm*—Lawrence L. Limpus

[57] ABSTRACT

A disposable active humidifier particularly for inspiratory lines of respiratory circuits for intensive care, comprising a body (2,2') provided with an inlet (3,3') and an outlet (4,4') for its connection along the inspiratory line and internally forming a chamber (10) for the flow of the gases of the inspiratory line, the humidifier further comprising a hydrophobic membrane (11) forming at least one portion of the surface of the chamber. The body (2,2') can be introduced by immersion in a water containment chamber (21) at least at the region affected by the membrane (11), the membrane being adapted to allow the passage of water in molecular form in the gas flow chamber (10).

11 Claims, 3 Drawing Sheets

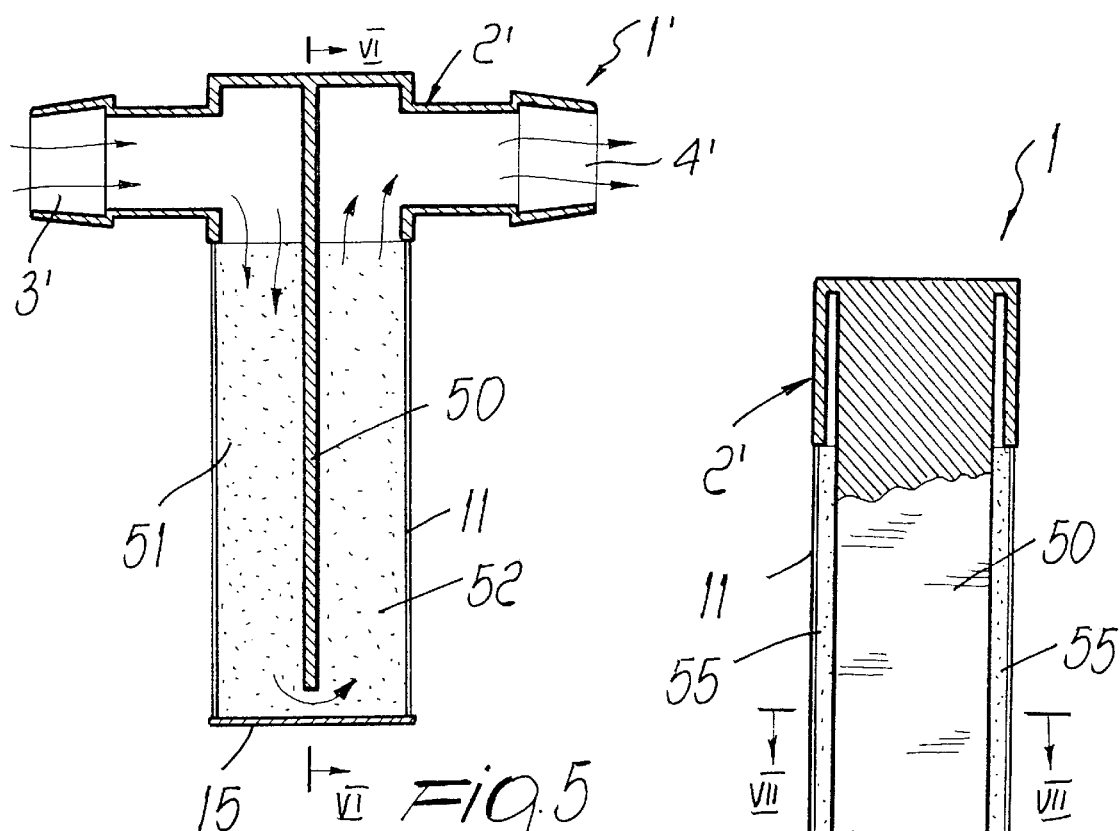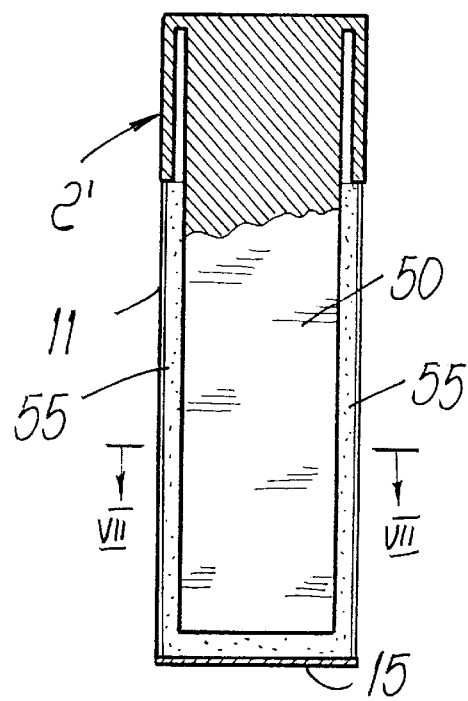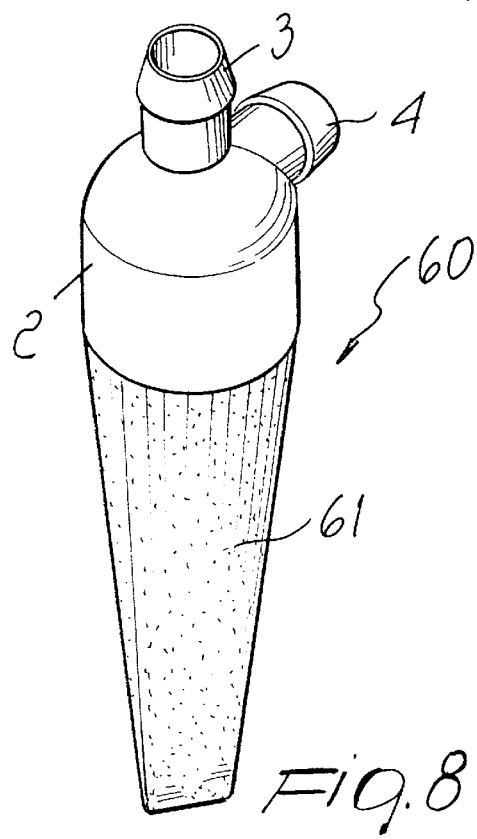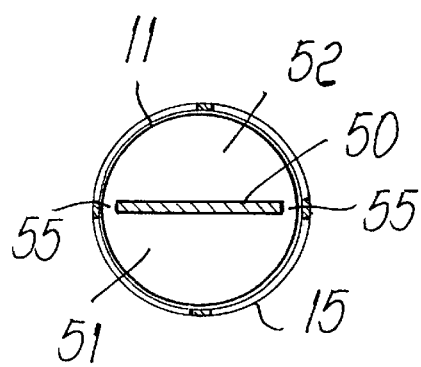

HEATED RESPIRATORY THERAPY HUMIDIFIER

TECHNICAL FIELD

The present invention relates to a disposable active humidifier, particularly for inspiratory lines of respiratory circuits for intensive care.

BACKGROUND ART

It is known that in intensive-care wards, where the patient is ventilated artificially with a respirator, heated humidifiers are usually used which are placed along the inspiratory line and are capable of providing a level of humidity and heat that the upper air passages of the patient, having been bypassed, cannot ensure, in order to maintain ordinary mucociliary functions.

Currently commercially available humidifiers heat the gases supplied by the ventilator and load them with humidity; in order to ensure the sterility of the inspiration gases, the water that is ventilated for humidification is necessarily sterile.

However, despite the use of sterile water, sterility conditions are not maintained, since in conventional active humidifiers the gas becomes loaded with humidity by flowing over the water surface. With this arrangement, the aerobic bacterial loads present in the incoming gases necessarily contaminate the heating bath.

The particular environmental condition, with the presence of humidity and heat, is the ideal medium for the proliferation of bacterial loads.

Furthermore, in addition to this type of contamination, the bath is also contaminated by means of the condensation that forms along the line that connects the humidifier to the patient; this condensation acts as a vehicle for the bacterial loads that are present in the air expired by the patient.

Accordingly, after a period of approximately two or three hours of operation, very high concentration of bacterial loads forms inside the humidification chamber; these loads constitute a severe risk of cross-infections for the patient.

With the conventional solutions, therefore, humidifiers are used which require the use of sterile water for their operation but do not allow to maintain sterility conditions.

U.S. Pat. No. 4,943,704 discloses a humidifier apparatus for admixture of heated water vapor into a gaseous stream, including a water heating platen, and a disposable vapor transfer chamber formed by a hydrophobic filter membrane supporting structure and a cover. The supporting structure is arranged over the water heating platen such that the filter is arranged above and extends parallel to the platen whereby heated water vapor rises through the filter and into the cover, which is provided with gas intake and discharge ports, to mix the heated water vapor into the gaseous stream.

DISCLOSURE OF THE INVENTION

A principal aim of the present invent on is to eliminate the drawbacks described above by providing a disposable active humidifier for inspiratory lines of respiratory circuits for intensive care that allows to heat and humidify the gas without having to necessarily use a sterile bath but at the same time with the assurance that any bacteria that may be present in the humidification and temperature-control water are not transmitted to the flow of gas that is inspired.

Within the scope of the above aim, a particular object of the invention is to provide a disposable active humidifier which, by modifying the conventional criteria for humidifying the flow of gas, allows to reduce the bacterial level that is present in the inspired gas, at the same time simplifying all the control and checking operations.

Another object of the present invention is to provide a disposable active humidifier that allows more efficient and immediate temperature regulation, by virtue of the fact that the amount of water to be heated is reduced significantly with respect to the amounts of water used in conventional humidifiers.

Another object of the present invention is to provide a disposable active humidifier that does not require connection to the external supply but is provided as a unit which is already preset for the amount of water that is sufficient for its use even for a prolonged time.

In accordance with a preferred aspect of the invention, there is provided a disposable active humidifier for inspiratory lines of respiratory circuits, which comprises a disposable cartridge including an elongated body provided at its upper end with an inlet and an outlet connected to an inspiratory line and being closed at its lower end. The body forms internally a gas flow chamber for flow of gases of the inspiratory line, and there is a hydrophobic membrane forming at least a portion of the lateral surface of the body and chamber between the upper end and lower end of the body. The elongated body is immersed in a water containment chamber at least at the region affected by the membrane which allows passage of water in a molecular form into the gas flow chamber.

BRIEF DESCRIPTION OF THE DRAWINGS

Further characteristics and advantages will become apparent from the following detailed description of some preferred but not exclusive embodiments of a disposable active humidifier particularly for inspiratory lines of respiratory circuits for intensive care, illustrated only by way of non-limitative example in the accompanying drawings, wherein:

FIG. 5 is a view of a cartridge of another preferred embodiment of the humidifier, with the inlet and the outlet for the gases arranged so that they are mutually aligned and opposite;

FIG. 6 is a sectional view of a cartridge, taken along the plane VI—VI of FIG. 5;

FIG. 7 is a sectional view, taken along the plane VII—VII of FIG. 6; and

FIG. 8 is a perspective view of a cartridge of other preferred embodiment of the invention.

WAYS OF CARRYING OUT THE INVENTION

Figure 1:
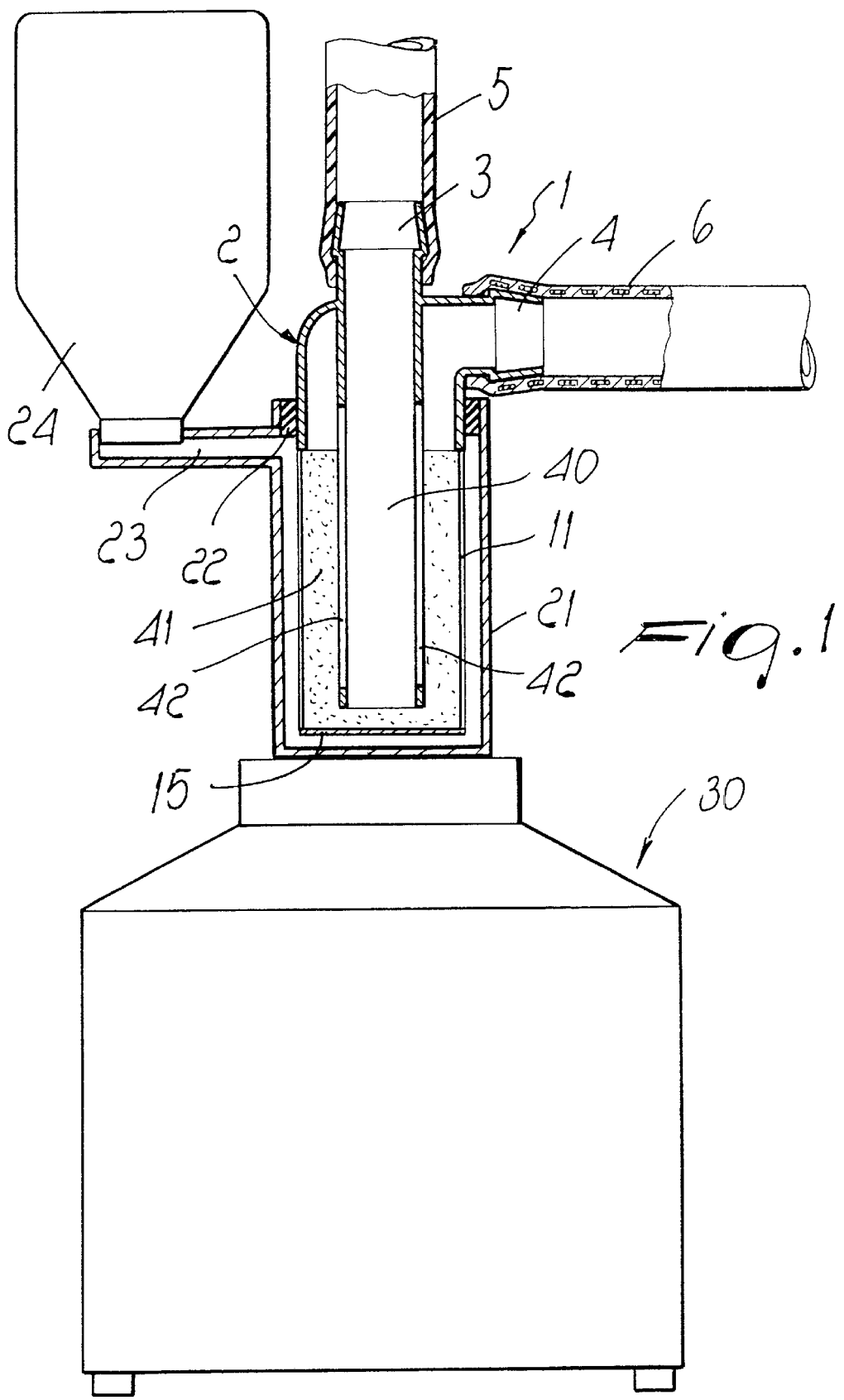
FIG. 1 is a schematic view of the active humidifier according to a preferred embodiment of the invention.
Figure 4:
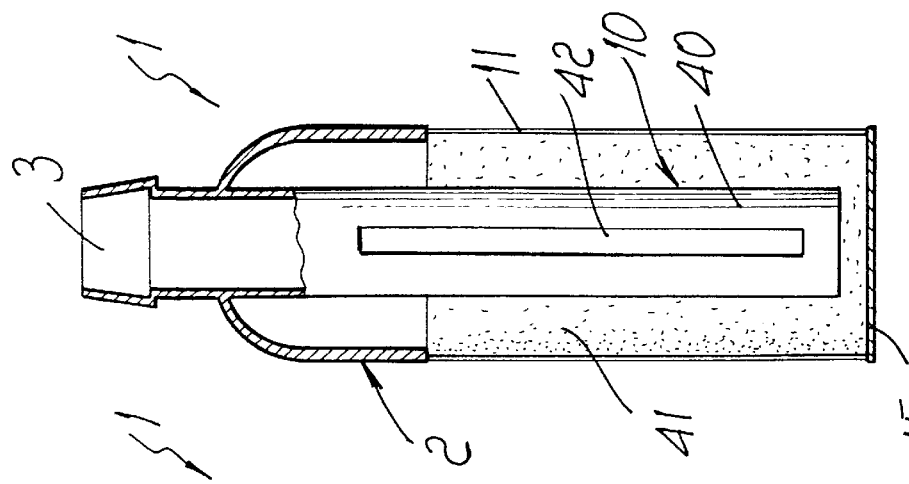
FIG. 4 is a sectional view, taken along a plane that lies at right angles to the sectional plane of FIG. 3.
Figure 3:
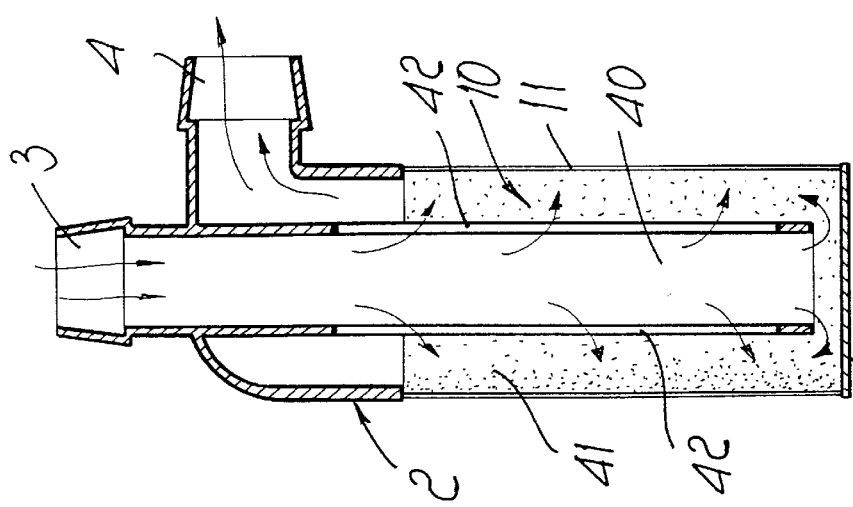
FIG. 3 is a sectional view, of the cartridge of FIG. 2 taken along an axial plane.
Figure 2:
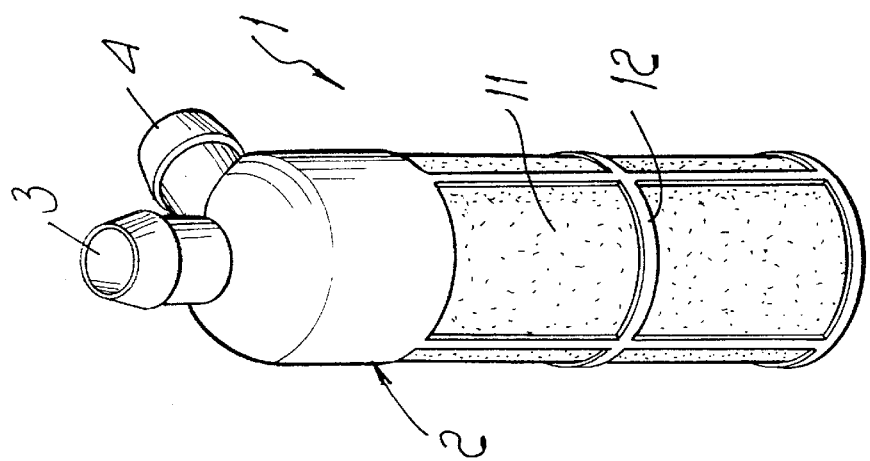
FIG. 2 is a perspective view of an interchangeable cartridge that constitutes the gas flow body of the humidifier of FIG. 1.

The disposable active humidifier particularly for inspiratory lines of respiratory circuits for intensive care of FIGS. 1–4 comprises a cartridge, generally designated by the reference numeral 1, constituted by a cylindrical body 2 provided with an axially arranged inlet 3 and with a radially arranged outlet 4; said inlet and said outlet allow to connect the cartridge alone an inspiratory line, which is constituted for example by a gas inlet tube 5 and by an outlet tube 6 that is connected to the patient.

The body 2 internally forms a chamber 10 for the flow of the gases of the inspiratory line.

An important particularity is constituted by the fact that the chamber 10 is formed by means of a hydrophobic membrane 11 that affects the lateral surface and is in practice supported by a cage-like grille 12 made of plastics that holds said membrane.

A closed bottom plate, designated by the reference numeral 15, is provided at the bottom.

In a similar manner, as shown in FIGS. 5 to 7, a cartridge is provided, designated by the reference numeral 1', wherein the body 2' has a gas inlet 3' and a gas outlet 4' that are mutually aligned and opposite.

The body 2 or 2', as shown in FIG. 1, is inserted in a water containment chamber 21 so that the membrane 11 is fully immersed in the liquid.

The chamber 21 is provided, in an upward region, with sealing gaskets 22 for engagement with the body 2 or 2', as well as with an upper branching duct 23, where the container 24 for introducing the water is arranged.

This arrangement causes new water to be introduced in the chamber 20 when the liquid of the chamber drops below the level at which the branching duct 23 is arranged.

The container 21 is preferably made of heat-conducting material and it can be applied above a heater, generally designated by the reference numeral 30, to heat the water.

The hydrophobic membrane 11, of a commercially available type, is constituted by a membrane having microscopic holes below a preset level and in practice allows the passage of water at the molecular level while preventing the passage of bacterial loads.

The membrane is arranged so as to affect the lateral surface of the gas flow chamber and is fully immersed in the liquid.

With this arrangement, the water containment chamber contains a very small volume of water, despite having a considerable surface of water in contact with the membrane, thus obtaining a considerable exchange surface with a limited volume of water that can accordingly be brought in a very short time to the temperature set by the thermostat-controlled heater.

In order to increase the exchange between the gases flowing into the inspiratory line and the membrane inside the gas flow chamber, there are flow channeling paths that can be provided, as shown in FIGS. 1 to 4, by an axial air injection channel 40 that opens proximate to the bottom, so as to create a return channel 41 arranged coaxially and so as to flow over the membrane more easily.

It is important to point out the fact that in order to prevent accidental obstructions of the gas flow, which might occur if water forms in the gas flow chamber, longitudinal slits, designated by the reference numeral 42, are provided on the inlet channel and in any case form a passage for the flow of gases even in the presence of water.

According to a different embodiment, illustrated in FIG. 5, the channeling paths are obtained by means of a diametrical dividing wall 50 forming a descending channel 51 and an ascending channel 52 arranged side by side, each one affecting a portion of the membrane; said channels are connected at the bottom region of the cartridge, proximate to the bottom plate 15.

In this case, too, to prevent obstruction of the gas flow if water is present inside the chamber 10, the dividing wall 50 is narrower than the diameter of the chamber, so that longitudinal slits 55 form which in any case allow the passage of the gas flow.

The gas outlet duct 6 is advantageously provided with a heating system and is provided with a double-walled tube, in which the resistor is inserted in the interspace between the two walls.

Therefore, with the above described arrangement, a single-use disposable cartridge is provided in which humidification is performed by means of water that need not be sterile, since the membrane 11 constitutes a diaphragm for the passage of the bacterial loads, which accordingly cannot pass from the liquid to the gas. Furthermore, the wide available surface, in relation to a limited volume of water, allows to significantly reduce thermal inertia, thus achieving a more rapid response to temperature regulation and allowing to significantly increase the surface for contact between the air and the membrane, said surface allowing both to humidify the air and to heat it.

FIG. 8 illustrates another preferred embodiment of the invention in which the cartridge, now designated by the reference numeral 60, can have a body 2 with connectors 3 and 4 to which a bag-shaped hydrophobic membrane 61 is connected.

In practice, the materials employed, so long as they are compatible with the specific use, as well as the contingent shapes and dimensions, may be any according to the requirements.

We claim:

1. A disposable active humidifier for inspiratory lines of respiratory circuits, comprising a disposable cartridge including an elongated body provided at its upper end with an inlet and an outlet connected to an inspiratory line and being closed at its lower end, the body forming internally a gas flow chamber for flow of gases of the inspiratory line, a hydrophobic membrane forming at least a portion of the lateral surface of said body and chamber between the upper end and lower end of said body, said body, being immersed in a water containment chamber at least at the region affected by said membrane, said membrane allowing passage of water in a molecular form into said gas flow chamber.

2. A disposable active humidifier according to claim 1, characterized in that said body has a substantially cylindrical shape and forms, at its lateral surface, a grille or cage for supporting said membrane.

3. A disposable active humidifier according to claim 1, characterized in that said water containment chamber is formed in a container made of heat-conducting material.

4. A disposable active humidifier according to claim 3, characterized in that said container that forms said water containment chamber has, proximate to its upper end, a branching duct for connection to a water supply duct.

5. A disposable active humidifier according to claim 1, characterized in that it comprises, inside said body, channels for the flow of the gases of the inspiratory line.

6. A disposable active humidifier according to claim 5, characterized in that said gas channels for the inspiratory line are provided by an axial inlet channel and by an outlet channel that is formed between said membrane and said inlet channel, said inlet channel being connected to said outlet channel proximate to the bottom of said body.

7. A disposable active humidifier according to claim 5, characterized in that said channels for the flow of the gases in said body are constituted by a diametrical dividing wall that forms, between an inlet and an outlet arranged mutually opposite, a descending channel and an ascending channel that are mutually connected proximate to the bottom of said gas flow chamber.

8. A disposable active humidifier according to claim 7, characterized in that it comprises, in said gas flow channels, slits adapted to allow the passage of the gases even if water is present inside said gas flow chamber of the inspiratory line.

9. A disposable active humidifier according to claim 6, characterized in that said axial gas inlet channel forms longitudinal slits arranged diametrically with respect to one another.

10. A disposable active humidifier according to claim 7, characterized in that said diametrical dividing wall is narrower than said gas flow chamber so as to form longitudinal slits for the passage of the gases.

11. A disposable active humidifier according to claim 1, characterized in that said body is provided with inlet and outlet connectors, to which a bag-shaped hydrophobic membrane is connected.

* * * * *